Figure 1:
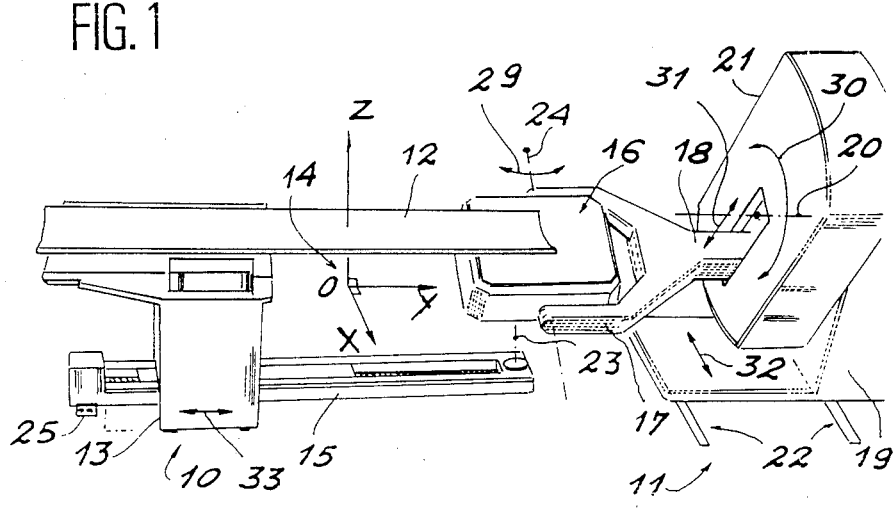

United States Patent [19]

Pare et al.

[11] Patent Number: 4,982,416
[45] Date of Patent: Jan. 1, 1991

[54] TABLE FOR SUPPORTING A PATIENT DURING EXAMINATION USING A SCINTIGRAPHIC INSTALLATION

[75] Inventors: Christian Pare, Plaisir; Christophe Fleury, Antony, both of France

[73] Assignee: Societe Nouvelle Informatek, Paris, France

[21] Appl. No.: 454,525

[22] Filed: Dec. 21, 1989

[30] Foreign Application Priority Data

Dec. 26, 1988 [FR] France .................. 88 17182

[51] Int. Cl.⁵ .............. G01T 1/66; G03B 42/02; H05G 1/00; H05G 1/02
[52] U.S. Cl. ............................ 378/20; 378/177; 378/208; 378/209; 378/179; 378/195; 378/68; 250/363.04; 250/363.02
[58] Field of Search ............... 378/177, 179, 178, 20, 378/208, 209, 195, 68, 69; 250/363.02, 363.05, 363.04, 363.08

[56] References Cited

U.S. PATENT DOCUMENTS

| | | | |
|---|---|---|---|
| 3,627,250 | 12/1971 | Pegrum | 248/324 |
| 3,777,124 | 12/1973 | Pavkovich | 378/68 |
| 4,012,636 | 3/1977 | Engdahl et al. | 250/363 |
| 4,652,758 | 3/1987 | Barfod | 250/363.05 |

FOREIGN PATENT DOCUMENTS 2213071 1/1974 France .

Primary Examiner—Edward P. Westin
Assistant Examiner—Don Wong
Attorney, Agent, or Firm—Walter C. Farley

[57] ABSTRACT

A scintographic installation includes a patient-supporting table (10) and a stand (11) whose support column (19) is moveable along an axis OX. The invention lies in the fact that the table (10) is mounted on a rail (15) which is capable of taking up different angular positions about an axis parallel to the axis OZ. In a first position the rail (15) is parallel to OY and the stand (11) is in a position suitable for performing tomographic examination. In a second position, the rail (15) is parallel to the axis OX and the stand (11) is a position suitable for examining the entire body by displacement of the column (19), i.e. without displacing the bed (12).

3 Claims, 1 Drawing Sheet

TABLE FOR SUPPORTING A PATIENT DURING EXAMINATION USING A SCINTIGRAPHIC INSTALLATION

The invention relates to installations for examining the human body using various different types of radiation, in particular X-radiation, gamma radiation, etc. In such installations, it relates more particularly to the tables provided for supporting a patient while still enabling the patient to be examined by instruments that may need to take up all sorts of appropriate positions around the patient.

In installations for radiological or scintigraphic examination, the patient to be examined lies on a bed of a material which is transparent to the radiation being used for the examination, e.g. a bed made of carbon fibers. This bed is mounted on a pedestal which generally includes various electromechanical devices for displacing the bed along three orthogonal axes, two horizontal axes X'X and Y'Y, are a vertical axis Z'Z. The apparatuses used for the examination per se are supported by arms driven with various motions, with said various motions serving to bring the examination apparatuses into the proximity of the patient and to enable them to scan the volume represented by the patient.

It will be understood that said scanning should not be impeded by any kind of obstacle, in particular the pedestal of the support table. That is why some installations have the bed mounted cantilevered out from the pedestal with the patient lying on the cantilevered portion.

In some installations, the examination apparatuses are mounted adjacent to the cantilevered portion on respective forks or clevises which are in turn carried at the ends of arms rotatable about a horizontal axes parallel to the longitudinal axis of the table to move around circumferences of various diameters. Each arm is carried by a vertical column capable of moving perpendicularly relative to the longitudinal axis of the table, thereby disengaging the cantilevered portion of the table so as to enable a patient to be placed thereon or removed therefrom, or else to give access to the patient when not actually examining the patient.

Such an installation is particularly well adapted to performing tomographic examination of the patient requiring circular, elliptical, or composite motion of the apparatuses around the bed. It is less well adapted to performing longitudinal examination of the patient from above and below since the arm cannot be displaced longitudinally. It is then necessary to displace the support table longitudinally which suffers from certain drawbacks. Firstly such displacement is disagreeable for the patient, and secondly it implies that the cantilevered bed supporting the patient is able to penetrate into the vertical column supporting the arm which therefore needs to have a tunnel formed therethrough. Another drawback is that such a system requires ground space to be available equal to twice the length of the bed.

Another way of examining the entire length of the body of a patient is to use a different method which consists in using a second bed disposed perpendicularly to the first while the cantilevered portion thereof is moved away from the arm. This second bed is carried by a longitudinal support which is fixed to a longitudinal stand extending along the ground beneath the bed. By this particular disposition, the examining apparatus carried by the arm can scan beneath the bed of the patient by displacing the support column on a rail disposed parallel to the bed.

Such an arrangement suffers from the major drawback of using two bulky beds and of giving rise to lost time when presenting one or other bed beneath the machine depending on the type of examination to be performed.

The object of the present invention is thus to provide a patient-supporting table suitable for performing tomographic examination or examination of the entire body.

The present invention provides a radiological or scintigraphic installation comprising a patient-supporting table constituted by a bed mounted to move on a pedestal along at least one direction parallel to a horizontal axis OY, the pedestal being moveably mounted on a rail on the ground disposed parallel to the bed, the installation further comprising a stand supporting at least one scintographic detector mounted on a column which is moveable in a direction parallel to a horizontal axis OX perpendicular to the axis OY, the installation being characterized in that the rail can take up at least two different angular positions about an axis parallel to a vertical axis OZ perpendicular to the horizontal axes OX and OY.

In a preferred embodiment, the first angular position corresponds to a rail extending parallel to the axis OY so as to enable the stand to perform to graphic examination, and the second position corresponds to a rail parallel to the axis OX, thereby enabling the stand to perform examination of the entire body by displacement of the column.

In addition, the various angular positions may be determined by abutments on the ground that co-operate with the rail.

Figure 2:
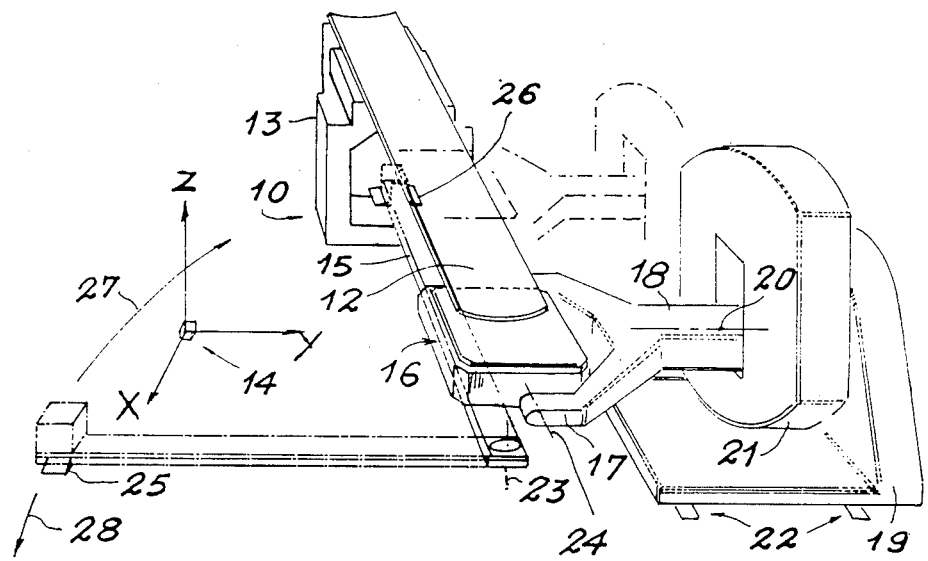

Other characteristics and advantages of the present invention appear from the following description of a particular embodiment, with the description being made with reference to the accompanying drawing in which:

FIG. 1 is a perspective view of an installation for scintigraphic examination including a support table of the invention in position for tomographic examination; and FIG. 2 is a similar view to FIG. 1 but showing the support table in position for examining the entire body.

The scintographic apparatus of the invention comprises an examination table 10 and a displacement device 11 for displacing the scintographic detector(s) and referred to as a stand. The examination table 10 comprises a bed 11 mounted on a pedestal 13. The bed and the pedestal 13 include conventional means (not shown) which co-operate to displace the bed along three orthogonal axes OX, OY, and OZ represented by a frame of reference 14. The pedestal 13 is slidably mounted on a rail 15 which is fixed to the ground parallel to the axis OY, thereby enabling the table to be moved along said axis (arrow 33) by means carried by the pedestal and not shown since they are conventional.

In the particular embodiment of FIGS. 1 and 2, the stand 11 supports a gamma ray detector which is pivotally mounted (arrow 29) about an axis 24 in a fork or clevis 17 at the end of an arm 18. The arm 18 is mounted on a vertical column 19 by means of a support 21 and is likewise pivotable about an axis 20 parallel to Y. The support 21 rotates abut the axis 20 (arrow 30) while the support end of the arm 18 moves in a vertical plane (arrow 31) parallel to the axis OX in order to change the radius at which the arm rotates. The vertical column 19 is slidably mounted on rails 22 by drive means (not shown). The rails 22 are disposed so as to enable the column 19 to move parallel to the axis OX and perpendicular to the axis OY (arrow 32).

At this point in the description, it will be observed that such an apparatus enables tomographic examination to be performed by rotating the detector 16 about the axis 20, with the radius of rotation being determined by the distance of the arm 18 from the axis. By displacing the bed in the direction OY, another portion of the body may be examined tomographically. However, in an installation as shown in FIG. 1, such displacement is limited by the length of the arm 18. As a result, in some installations, the support 21 has a tunnel formed therethrough as mentioned in the introduction, thereby making it possible to examine an entire body displacing the table in conventional manner. Such an installation with a tunnel suffers from the drawbacks mentioned in the introduction.

In an installation without a tunnel, as shown in FIG. 1, an entire body is usually examined by means of a special second bed which is disposed parallel to the axis OX and which enables the detector 16 to move longitudinally without obstruction beneath the bed by displacing the column 19 on the rails 22.

The invention proposes a different solution which is to cause the table 10 to pivot through 90° so as to bring the bed into a position where it is parallel to the axis OX while remaining within the field of the instrument 16. FIG. 2 shows this new position for the table 10 relative to the stand 11. The table is rotated by means of a rail 15 which is pivotally mounted about a vertical axis 23. The vertical axis 23 is situated, for example, in a vertical plane containing the axis 24 which corresponds to the mid axis of the detector 16. The exact position of said axis 23 on the ground is determined as a function of the end limits for displacement of the column 19 on the rail 22.

With the stand 11 and the table 10 in the respective positions shown in FIG. 2, an entire body can be examined by displacing the stand 11 along the rails 22 (position shown in dot-dashed lines in FIG. 2). It is therefore necessary to place the axis 23 so that such examination is possible without displacing the bed 12 relative to the pedestal 13. It is also necessary for the position of the axis to allow tomographic examination to be performed when the items are in the relative positions shown in FIG. 1.

In order to enable the table 10 to be moved accurately between its two positions at 90° from each other, these two positions are delimited by abutments on the ground referenced 25 for the FIG. 1 position and 26 for the FIG. 2 position. These abutments 25 and 26 are naturally fastening devices for the rail so as to keep it in a fixed position over time.

In FIG. 2, displacement is shown in the direction of an arrow 27, but it is equally possible to choose displacement in the direction of an arrow 28, in which case a corresponding abutment would be required and it may be necessary to find a different position for the axis 23.

Naturally, in applications other than those shown in FIGS. 1 and 2, it would be possible to choose other angular positions differing by 90° for the rail 15 about the axis 23 depending on requirements and convenience for performing examinations.

The invention is described in an application for use with scintographic apparatus, however it is equally applicable to radiological apparatuses, in particular.

We claim:

1. A scintographic installation comprising a patient-supporting table (10) constituted by a bed (12) mounted to move on a pedestal (13) along at least one direction parallel to a horizontal axis OY, the pedestal being moveably mounted on a rail (15) on the ground disposed parallel to the bed (12), the installation further comprising a stand (11) supporting at least one scintographic detector (15) mounted on a column (11) which is moveable in a direction parallel to a horizontal axis OX perpendicular to the axis OY, the installation being characterized in that the rail (15) can take up at least two different angular positions about an axis (23) parallel to a vertical axis OZ perpendicular to the horizontal axes OX and OY.

2. A scintographic installation according to claim 1, characterized in that the first angular position corresponds to a rail (15) extending parallel to the axis OY so as to enable the stand (11) to perform tomographic examination, and in that the second position corresponds to a rail (15) parallel to the axis OX, thereby enabling the stand to perform examination of the entire body by displacement of the column (19).

3. A scintographic installation according to claim 1 or 2, characterized in that it further includes at least two abutments on the ground determining the various angular positions of the rail (15).

* * * * *